United States Patent [19]

Vrouenraets et al.

[11] Patent Number: 4,938,752

[45] Date of Patent: Jul. 3, 1990

[54] ABSORBENT SANITARY PRODUCTS

[75] Inventors: Cornelius M. F. Vrouenraets, Dieren; Hans R. Herberts, Drempt, both of Netherlands

[73] Assignee: Akzo N. V., Arnhem, Netherlands

[21] Appl. No.: 256,920

[22] Filed: Oct. 12, 1988

[30] Foreign Application Priority Data

Oct. 12, 1987 [NL] Netherlands ................ 8702422

[51] Int. Cl.[5] ............................................. A61F 13/18
[52] U.S. Cl. .................................... 604/370; 428/286; 428/913
[58] Field of Search ................ 604/370–373, 604/378; 428/327, 480, 913, 296

[56] References Cited

U.S. PATENT DOCUMENTS

| | | | |
|---|---|---|---|
| 3,968,183 | 7/1976 | Hayashi et al. | 260/860 |
| 4,047,534 | 9/1977 | Thomaschefsky et al. | 604/370 |
| 4,324,246 | 4/1982 | Mullane | 604/370 |
| 4,493,870 | 1/1985 | Vrouenraets et al. | 428/245 |

FOREIGN PATENT DOCUMENTS

| | | |
|---|---|---|
| 0192965 | 9/1986 | European Pat. Off. |
| 2634994 | 2/1977 | Fed. Rep. of Germany |
| 2750900 | 6/1978 | Fed. Rep. of Germany |
| 2751822 | 6/1978 | Fed. Rep. of Germany |
| 51-111290 | 10/1976 | Japan |
| 682866 | 11/1952 | United Kingdom |
| 1403210 | 8/1975 | United Kingdom |
| 1404340 | 8/1975 | United Kingdom |

OTHER PUBLICATIONS

Kirk–Othmer, *Encyclopedia of Chemical Technology*, vol. 9, pp. 232–241.

*Primary Examiner*—Jerome L. Kruter
*Attorney, Agent, or Firm*—Oliff & Berridge

[57] ABSTRACT

Absorbent sanitary products, such as diapers, pads, or sanitary napkins, comprising a copolyether ester film having a water permeability of at most 0.02 g/cm$^2$/h at 23° C. and 0.07 bar and a water vapor permeability of at least 500 g/m$^2$/day at 23° C. and 100–50% relative humidity, a liquid-permeable layer, and a liquid-absorbing bibulous layer. The copolyether ester of the film contains 5–55 weight % of long-chain glycols having a molecular weight of 800–6000 with an atomic ratio of carbon to oxygen of 2.0 to 3.7 %. The film is made from copolyether ester chips which in water at 23° C. have a water absorption of at most 15 weight %.

8 Claims, No Drawings

ABSORBENT SANITARY PRODUCTS

TECHNICAL FIELD

The invention relates to an absorbent sanitary product, such as a diaper, pad, or sanitary napkin, comprising (1) a film having a low liquid permeability and a water vapor permeability of at least 500 g/m²/day at 23° C., 100–50% relative humidity and wind velocity 0.3m/s, (2) a liquid-permeable layer, and (3) a liquid-absorbing bibulous layer. The film is made of a copolyether ester, which consists of a large number of recurrent intralinear ester groups having long-chain ester units and ester groups having short-chain ester units, which are randomly joined head-to-tail through ester bonds. The ester groups having longchain ester units correspond to the following formula:

and the said ester groups having short-chain ester units correspond to the following formula:

In the above formulae, G is a bivalent radical remaining after removal of terminal hydroxyl groups from at least one long-chain glycol having a molecular weight greater than 800 and an average atomic ratio of carbon to oxygen of 2.0 . R is a bivalent radical remaining after removal of carboxyl groups from at least one dicarboxylic acid having a molecular weight less than 300. D is a bivalent radical remaining after removal of hydroxyl groups from at least one diol having a molecular weight less than 250. At least 75 mole % of the dicarboxylic acid consists of terephthalic acid or the ester-forming equivalents thereof. At least 75 mole % of the low-molecular-weight diol consists of 1,4-butanediol or the ester-forming equivalents thereof. The sum of the mole percentages of the dicarboxylic acid which is not terephthalic acid or an ester-forming equivalent thereof, and of the low-molecular-weight diol which is not 1,4-butanediol or an ester-forming equivalent thereof, is at most 25.

BACKGROUND OF THE INVENTION

A sanitary product with a corresponding film is already known from Unexamined Japanese Patent Application 51/111,290, the copolyether ester being made of long-chain and short-chain ester units and the short-chain ester units comprising 30–40 weight % of the copolyether ester and the long-chain ester units being terephthalic acid and polyethylene glycol having a molecular weight of 800 to 3000.

European Patent Application 192,965 discloses a similar product, in which the nearly liquid-impermeable but water-vapor-permeable film is a monoaxially stretched porous film of a polyolefin having a thickness of at most 60 $\mu$, a pore size between 0.05 and 5 $\mu$, a pore volume of at least 0.1 cm³ per cubic centimeter of film, a water vapor permeability of at least 500 g/m²/day, and a flexural strength (in mm) corresponding at most to 0.193 times the film thickness (in $\mu$) +35.

Although the products described therein constitute an improvement over prior-art water-vapor-impermeable products, there is a great need for absorbent sanitary products with improved properties, e.g., a higher water-vapor permeability with an identical or higher waterproofness.

In U.S. Pat. 4,493,870 a portion of the copolyether esters used in the present invention is recommended for the manufacturing of films for use in waterproof rainwear and tents. The majority of the copolyether ester films described in the examples, however, are not suitable for the manufacture of absorbent sanitary products, because the films are too water-permeable under conditions that may occur during use of sanitary products. It appears that very high requirements for the suppleness of the material are imposed on films for use in sanitary products. Finally, the manufacturing costs for these films must be reasonable.

An absorbent sanitary product has now been found through the invention, the said product possessing the above-mentioned improved properties, which are realized moreover in a simple manner.

SUMMARY OF THE INVENTION

The invention is characterized in that the absorbent sanitary product of the above-mentioned type contains a film of copolyether ester, 45-95 weight % of the ester groups in that ester consisting of short-chain ester units. The film's liquid permeability is a maximum of 0.02 g/cm²/h at 23° C. and 0.07 bar. The percentage by weight of the long-chain-chain ester units in the copolyether ester comprises 5-55%. The average atomic ratio of carbon to oxygen of the long-chain glycol is 2.0 to 3.7, with the proviso that if the average atomic ratio of carbon to oxygen of the long-chain glycols is 2.0 to 2.4, the percentage by weight of the long-chain ester units is 5-35%. The copolyether ester film is manufactured by flat-sheet extrusion or extrusion blow molding from polymer chips, which in 23° C. water exhibit a water absorption of at most 15 weight %, referred to the dry weight of the chips.

DETAILED DESCRIPTION OF PREFERRED EMBODIMENTS OF THE INVENTION

In addition to the copolyether ester films with the above-stated properties, the novel sanitary products contain a layer which is water-permeable to a high degree. The said layer generally consists of a woven or nonwoven product made of a preferably hydrophobic material. In this case, a nonwoven product made of a polyolefin, e.g., polyethylene and especially polypropene or copolymers thereof, is preferred. Other options include preferably nonwoven products made of other hydrophobic materials, e.g., polyester.

For the preparation of copolyether esters for use in the novel absorbent sanitary products, reference is made to British Pat. No. 682,866, 1,403,210, and 1,404,340.

Preferably copolyether esters containing 60–90 weight % of short-chain ester units are used for the novel absorbent sanitary products.

A polyalkylene oxide glycol having a molecular weight of 1000 to 5000 is used preferably as the glycol for the formation of long-chain ester units having an average atomic ratio of carbon to oxygen of 2.0–3.7.

Within the scope of the present invention, copolyether esters are preferred having ester groups with short-chain ester units consisting entirely or substantially of polybutyleneterephthalate groups. Films of such copolyether esters are easy to prepare. Moreover, films made of this material generally show better technical properties in the application under discussion than films of copolyether esters in which, for example, 25% of the terephthalic acid has been replaced by another dicarboxylic acid. In special applications, the replacement of a small portion of 1,4-butanediol by another diol and/or the replacement of terephthalic acid by another low-molecular-weight dicarboxylic acid may be advantageous Low-molecular diols (other than 1,4-butanediol) which are converted into short-chain ester groups include acyclic, alicyclic, and aromatic dihydroxy compounds. Preferred are diols with 2–15 carbon atoms, e.g., ethylene, propylene, isobutylene, pentamethylene, 2,2-dimethyltrimethylene, hexamethylene, and decamethylene glycol, dihydroxycyclohexane, cyclohexane-dimethanol, resorcinol, hydroquinone, and 1,5-dihydroxynaphthalene. Particularly preferred are aliphatic diols having 2–8 carbon atoms.

Suitable bisphenols include bis(p-hydroxy)-diphenyl, bis(p-hydroxyphenyl)methane, and bis(p-hydroxyphenyl)-propane. Corresponding ester-forming derivatives of diols are likewise suitable (e.g., expoxyethane or ethylene carbonate can be used instead of ethylene glycol). The term "low-molecular-weight diols" refers to such corresponding ester-forming derivatives, the molecular weight requirement, however, referring to the diol itself and not to the derivatives thereof.

Dicarboxylic acids (other than terephthalic acid) which are reacted with the indicated long-chain glycols and with lowmolecular-weight diols to form copolyesters include aliphatic, cycloaliphatic, and aromatic dicarboxylic acids having a molecular weight up to 300. In this context, the term "dicarboxylic acid" is understood to also include equivalents of dicarboxylic acids having two functional carboxyl groups, the behavior of which is practically the same as that of dicarboxylic acids during reaction with glycols and diols to form copolyesters. These equivalents include esters and ester-forming derivatives, e.g., acid halides and anhydrides. The molecular weight requirements refer to the acid and not to the equivalent ester or the ester-forming derivatives thereof. The dicarboxylic acids can include any substituted groups or combinations, which do not detrimentally affect copolyester formation and the use of the polymer in the elastomeric products according to the present invention. In this context, the term "aliphatic dicarboxylic acids" refers to carboxylic acids with two carboxyl groups, each of which is attached to a saturated carbon atom. Aliphatic or cycloaliphatic acids having conjugated unsaturated bonds frequently cannot be used because of homopolymerization. Some unsaturated acids, e.g., maleic acid, are suitable however. In this context, the term "aromatic dicarboxylic acids" refers to dicarboxylic acids having two carboxyl groups, which are attached in each case to a carbon atom of a benzene ring or a polynuclear aromatic ring system. It is not necessary for both functional carboxyl groups to be attached to the same aromatic ring. If several rings are present, they can be joined by aliphatic or aromatic or other bivalent groups, e.g., —O— or —SO$_2$—. Cyclohexanedicarboxylic acids and adipic acid are used preferably.

Suitable aromatic dicarboxylic acids include phthalic and isophthalic acids, bisbenzoic acid, substituted dicarboxyl compounds with two benzene rings, e.g., bis(p-carboxyphenyl)methane, p-oxy(p-carboxyphenyl)benzoic acid, ethylene-bis(p-oxybenzoic acid), 1,5-napthalenedicarboxylic acid, 2,6-naphthalenedicarboxylic acid, 2,7-naphthalenedicarboxylic acid, phenanthrenedicarboxylic acid, anthracene dicarboxylic acid, 4,4'-sulfonyl-dibenzoic acid, and derivatives thereof with alkyl groups having 1–12 carbon atoms and ring-substituted derivatives, e.g., halogen, alkoxy, and aryl derivatives. Hydroxy acids, e.g., p-(beta-hydroxyethoxy)benzoic acid can likewise be employed with the proviso that an aromatic dicarboxylic acid is also present.

When preparing the copolyesters, aromatic dicarboxylic acids are employed preferentially, particularly acids with 8–16 carbon atoms, above all phenylenedicarboxylic acids, i.e., phthalic and isophthalic acids.

According to the invention, the long-chain glycol must have an average atomic ratio of carbon/oxygen of 2.0 to 3.7. In this case, one can use only a polyalkylene oxide glycol having a carbon to oxygen ratio of 2.0 to 3.7, or a mixture of a polyethylene oxide glycol having a carbon to oxygen ratio of 2.0 with a polyalkylene oxide glycol having a higher carbon to oxygen ratio, the ends, for example, being blocked by polyethylene oxide groups. Also suitable is a polyalkylene oxide glycol, which is obtained by heteropolymerization of ethylene oxide and a second epoxy alkane monomer. The proportion of the second monomer in polyalkylene oxide glycol is preferably less than 80 mole % or, if the average atomic ratio of carbon to oxygen is 2.0 to 2.4, less than 20 mole %. Suitable examples of the second monomer are 1,2- and 1,3-epoxypropane, 1,2-epoxybutane, and tetrahydrofuran.

The carbon to oxygen ratio of 2.0 in the long-chain glycols within the scope of the invention produces suitable copolyesters only if the proportion of short-chain ester units is high, because otherwise the water absorption of the polymer chips exceeds 15 weight %, which at the same time results in deterioration of waterproofness. If the proportion of short-chain ester units is reduced, then the carbon to oxygen ratio in the polyalkylene glycol must be raised to 3.7 by the addition of another polyether monomer, to ensure the low water absorption of polymer chips and waterproofness of the copolyester film.

The polymers described herein can be prepared in a simple manner by conventional transesterification. In a preferred process, terephthalic acid dimethyl ester is heated to 150–260° C. with a long-chain glycol and a molar excess of butanediol with use of a catalyst, after which the methanol formed during transesterification is distilled off. Heating is continued until methanol evolution ceases. The transesterification occurs within a few minutes to several hours, wherein the duration depends on the temperature, the type of catalyst, and the diol excess This process produces a low-molecularweight copolyester according to the process described below. Such prepolymers can also be prepared by a number of other esterification or transesterification processes; the long-chain glycol can be reacted, for example, with a homopolymer or a copolymer of a short-chain ester having a high or low molecular weight with the use of a catalyst, until random distribution occurs. Homopolymers or copolymers of esters with short-chain ester units can be prepared by transesterification from dimethyl esters and lowmolecular-weight diols, as described herein, or from free acids with diol acetates. The ester copolymer with short-chain ester units can be prepared likewise by direct esterification from suitable acids, anhydrides, or acid chlorides, e.g., with diols, or by other processes, e.g., by reaction of the acids with cyclic ethers or carbonates. The prepolymer is also obtained by running this process in the presence of a long-chain glycol.

The resulting polymer is then converted to a high-molecular-weight product by distilling off the excess diol having short-chain molecules. This process is known as "polycondensation." Additional transesterification occurs in the said distillation to increase molecular weight and to achieve randomization of the copolyester groups. The best result is usually obtained if this end distillation or polycondensation is run at a pressure of at most 130 Pa and at 240–260°C. for at most 2 hours in the presence of an antioxidant, e.g., sym.di-beta-naphthyl-p-phenylenediamine and 1,3,5-trimethyl-2,4,6-tris[3,5-di-tert-butyl-4-hydroxy-benzyl]-benzene. The polymerization technique with the greatest practical significance is transesterification, which is used to end the polymerization reaction. To avoid exposing the products to high temperatures for too long with the consequence of a possibly irreversible thermal degradation, it is expedient to use a catalyst in the transesterification. A great many catalysts are suitable for this purpose; used preferentially, however, are organic titanates, e.g., tetrabutyl titanate, used alone or in combination with magnesium or calcium acetate. Complex titanates, e.g., $Mg[HTi(OR)_6]_2$, which are prepared from alkali or alkaline earth metal alkoxides and titanate esters, are likewise highly suitable. Inorganic titanates, e.g., lanthanum titanate, calcium acetate/antimony trioxide mixtures, and lithium and magnesium alkoxides are examples of other catalysts that can be used as well.

According to the invention, a glycol with a molecular weight of 800 to 6000 is always used as the long-chain glycol.

When a glycol with a molecular weight less than 800 is used, an unacceptable high amount of glycol has to be incorporated by the copolyether esters. A film made therefrom having a thickness of, for example, 35 μm and a water vapor permeability of at least 500 g/m²/day at 23°C., 100–50% rel. humidity and a wind velocity of 0.3 m/s proved to be less suitable for use in absorbent sanitary products because of its technical properties. The manufacturing of absorbent products with copolyether ester films of copolyether esters prepared with a glycol with a molecular weight greater than 6000 also produces unsatisfactory results, because the technical properties of the copolyether ester films in part do not satisfy requirements, e.g., relative to strength.

Both water permeability and also water vapor permeability of the copolyether ester films to be used in the said products depend not only on their formulation but on their thickness as well. For each selected film thickness, water permeability may be at most 0.02 g/cm²/h at 23°C. and 0.07 bar, whereas water vapor permeability must be at least 500 g/m²/day at 23°C., 100–50% rel. humidity and wind velocity 0.3 m/s. It appeared that very good results are achieved with the use of a polymer film with a thickness of 5 to 35 μm. An optimal result is attained in general with a polymer film thickness of 10 to 15 μm.

The manufacture of films from the present copolyether esters is carried out according to the process known per se, as described in Kirk-Othmer, Encyclopedia of Chemical Technology, Vol. 9 (1966), pp. 232–241.

Films with a thickness of 5 to 35 cm may be manufactured by extrusion blow molding.

Preferred are flat films obtained by flat-sheet extrusion on a chill roll. The roll temperature is preferably 40 to 120°C, as described in U.S. Patent No. 3,968,183.

The films made by the above-described process generally have a lower water absorption capacity than films obtained in other ways, for example, by compression molding.

Water absorption was determined with use of the chips. The procedure was as follows: Copolyether ester chips, about 3 mm long and 2.5 mm in diameter, were placed for a week in water with a temperature of 23°C. After thorough removal of adhering moisture by filter paper, the amount of water absorbed was determined by weighing.

In the manufacture of absorbent sanitary products according to the present invention, good results are achieved with copolyether ester films made by flat-sheet extrusion and/or extrusion blow molding from polymer chips, which after being kept in water at 23°C have a water absorption of at most 15 weight %, referred to the dry weight of the chips.

In this case, polymers are preferred in which the chips made therefrom absorb at most 12 weight % of water. Absorbent materials known from sanitary products can be used as the liquid-absorbing bibulous layer in the novel sanitary products.

This type of bibulous layer in many instances consists of kraft pulp inserted into a nonwoven product.

Essential for good properties and high wear comfort of an absorbent sanitary product are the absorption properties of the bibulous layer, in addition to the high waterproofness of the water-impermeable film. There are characterized by liquid absorption, liquid retention, and rewetting.

The measurement of liquid absorption is carried out according to DIN 53923.

For this purpose, synthetic urine or synthetic blood were used as test liquids. Synthetic urine has the composition:

| | |
|---|---|
| NaCl | 10 g |
| Urea | 24 g |
| $MgSO_4$ | 0.6 g |
| Ca acetate | 0.7 g |
| Distilled water | 964.7 g |

The surface tension of this type of synthetic urine is about 48 mN/m.

Synthetic blood for testing the bibulous layer has the composition:

| | |
|---|---|
| NaCl | 10 g |
| Na carbonate | 10.7 g |
| Glycerol | 100.0 g |
| Carboxymethylcellulose | 4.6 g |
| Distilled water | 874.7 g |

The surface is about 46 mN/m, and viscosity about 10 m·Pas.

The Demand Wettability Test fulfills the requirements for practical testing especially well. In so doing, a device is used by which the volume and rate of absorption of a liquid are measured by adjusting the absorbing material to a hydrostatic pressure of zero, so that wetting occurs only according to the demand of the absorbing material. Liquid absorption occurs only due to the capacity of the absorbing material to absorb liquid, wherein the liquid stream stops immediately once the saturation point has been reached. The fibrous pulp can be prepared to simulate the actual end product (cf. "Nonwoven Product Technology," International Nonwovens and Disposables Association, New York, 1974, 129–142).

Rewetting (WET Beck Test) is measured as follows:

0.8 g of the absorbing material is uniformly distributed over a surface of 100 cm$^2$ (10 cm x 10 cm), and 16 ml of a 1% NaCl solution is poured over it. After 3 minutes, the surface is covered with paper filter layers, 11 cm x 11 cm in size (about 20 g), and the surface is weighed down with 35 g/g. The liquid absorption by the filter paper, determined after 3 minutes, is equivalent to the rewetting.

To assure high wear comfort, preferably such bibulous layers are used in which the bibulous layer has a liquid absorption of at least 5 g/g, measured according to DIN 53923, a retention capacity of at least 3 g/g according to the Demand Wettability Test, and a rewetting of at most 10% of the absorbed liquid.

The characteristic properties, especially advantageous for the novel absorbent sanitary products, of the bibulous layer, which together with the copolyester film satisfies high quality requirements, are preferably achieved in that the bibulous layer contains polymers with a very high water absorption capacity. Suitable products have been disclosed, for example, in DE 26 34 994-C2, DE 27 50 900-A1, and DE 27 51 822-A1.

In general, these refer to modified cellulose and/or salts of cross-linked polyacrylates.

In addition to the abovementioned components, the novel sanitary products can also contain pressure-sensitive strips for fixing the bibulous layer. To increase wear comfort and to prevent the escape of liquid, strips made of an elastic material can also be used.

The following methods are used to determine the properties of copolyether ester films designated for the novel sanitary products:

(A) Determination of Waterproofness WP:

For this purpose, a circular sample of the film to be analyzed with a diameter of 6.15 cm is placed between a water-absorbing layer and a filter paper of the same size. Used as the water-absorbing layer is 1 g of a polymer with a very high water absorption capacity, which was saturated with 5 g of water and has been placed between two paper tissues. The paper tissue that is not on the film side is covered with a layer of a hydrophobic nonwoven material.

The increase in weight of the filter paper after 5 min under a weight of 2 kg, uniformly distributed over the product to be analyzed on the side of the nonwoven material, is a measure of the waterproofness.

(B) Determination of Water Vapor Permeability:

Introduced into a cell with a diameter of 5.6 cm is 3 g of a polymer with a very high water absorption capacity ("superslurper"), the said polymer having been saturated with 20 g of water. The film to be analyzed is then stretched over the polymer such that it is well moistened by the said polymer. The decline in weight per hour at a temperature of 23°C, a relative humidity of 50%, and a wind velocity of 0.3 m/s is a measure of water vapor permeability.

(C) The water uptake of the polymer chips is determined at 23°C.

EXAMPLE I

Introduced into a 200-L autoclave were 37.6 kg of dimethyl terephthalate, 24.4 kg of 1,4-butanediol, and 7.5 kg of polyethylene oxide glycol having an average molecular weight of 4000. The reaction mixture was heated to 110°C with stirring, and then 500 ppm tetrabutyl titanate (referred to dimethyl terephthalate) was added. Methanol was distilled off with a further increase in temperature to 160°C, after which the pressure was slowly reduced to 100 Pa and the temperature raised to 245°C. During this polycondensation reaction, lasting 3 to 4 hours, a product was formed having a relative viscosity of 2.14 (measured at a concentration of 1.0 g in 100 g of m-cresol at 25°C.)

A number of copolyether esters with different amounts of the specified polyethylene oxide glycol (PEG) and optionally polytetrahydrofuran (PTHI.) having an average molecular weight of 1000 is obtained in a way similar to that described hereinabove.

The copolyether esters prepared had the following compositions:

TABLE 1

| Wt % of short-chain ester groups | Wt. % of PEG | Wt. % of PTHF | η rel after polycondensation | η rel after post polycondensation | Water absorp. g/g |
|---|---|---|---|---|---|
| A 84.5 | 15 | 0 | 2.14 | 3.48 | 6.2 |
| B 78.8 | 15 | 5 | 2.24 | 3.91 | 9.1 |
| C 67.5 | 15 | 15 | 2.46 | 4.56 | 11.1 |
| D 79.3 | 20 | 0 | 2.21 | 4.02 | 10.2 |
| E 73.7 | 20 | 5 | 2.32 | 4.19 | 12.2 |
| F 68.0 | 20 | 10 | 2.43 | 4.43 | 14.7 |
| G 69 | 31 | 0 | — | — | 17.1 |

EXAMPLE II

The copolyether esters prepared according to Example I were processed into films 15 μ thick (copolyether esters E, F, and G also into films 10 μ thick), after which water vapor permeability (WVP) and waterproofness (WP) were determined. The test results are reproduced in the table below.

TABLE 2

| Polymer | Wt. % PBTP | η rel of film | WVP (g/m$^2$/24 h) at film thickness 10 μm | WVP (g/m$^2$/24 h) at film thickness 15 μm | WP (g/cm$^2$/h) at film thickness 10 μm | WP (g/cm$^2$/h) at film thickness 15 μm |
|---|---|---|---|---|---|---|
| A | 84.5 | 2.67 | — | 650 | — | 0.003 |
| B | 78.8 | 2.81 | — | 890 | — | 0.005 |
| C | 67.5 | 3.09 | — | 1760 | — | 0.006 |
| D | 79.3 | 2.61 | — | 1320 | — | 0.007 |
| E | 73.7 | 2.79 | 2700 | 1990 | 0.014 | 0.011 |
| F | 68.0 | 2.91 | 3200 | 2830 | 0.020 | 0.017 |
| G | 69 | 3.5 | 4100 | 3490 | 0.030 | 0.034 |

Comparison measurements with a commercial product based on microporous polyethylene yielded a water vapor permeability of 1060 g/m$^2$/24 h and a waterproofness of 0.006 g/cm$^2$/h.

The results in the table above indicate that films with a waterproofness WP less than or equal to 0.02 g/cm$^2$/h and a water vapor permeability WVP greater than 500 g/m$^2$/24 h are obtained from polymers A to F. They are eminently suitable for absorbing sanitary products.

Polymer G is a polymer, from which according to U.S. Pat. No. 4,493,870 a film was prepared for manufacturing rainwear or tents. This type of film is less suitable for use in the novel sanitary products because of its relatively high water permeability. A clearly thicker film must be used in such products to meet the requirements for tightness of the film, and this can reduce the desired wear comfort, apart from the fact that the quantity of material used is substantially higher.

WHAT IS CLAIMED IS:

1. An absorbent sanitary product, comprising:

a film having a water vapor permeability of at least 500 g/m$^2$/day at 23°C., 100–50% relative humidity and wind velocity 0.3 m/s, a liquid-permeable layer, and a liquid-absorbing bibulous layer;

said film comprising a copolyether ester which consists of a plurality of recurrent intralinear ester groups having long-chain ester units and ester groups having short-chain ester units, which are randomly joined head-to-tail through ester bonds;

said ester groups having long-chain ester units corresponding to the formula:

and said ester groups having short-chain ester units corresponding to the formula:

wherein:

G is a bivalent radical remaining after removal of terminal hydroxyl groups from at least one long-chain glycol having a molecular weight greater than 800 and an average atomic ratio of carbon to oxygen of 2.0, R is a bivalent radical remaining after removal of carboxyl groups from at least one dicarboxylic acid having a molecular weight less than 300, and D is a bivalent radical remaining after removal of hydroxyl groups from at least one low-molecular-weight diol having a molecular weight less than 250;

at least 75 mole % of said dicarboxylic acid consisting of terephthalic acid or ester-forming equivalents thereof and at least 75 mole % of said low-molecular-weight diol consisting of 1,4-butanediol or ester-forming equivalents thereof, and a sum of the mole percentages of the dicarboxylic acid which is not terephthalic acid or an ester-forming equivalent thereof, and of the low-molecular-weight diol which is not 1,4-butanediol or an ester-forming equivalent thereof is at most 25;

45 to 95 weight % of the copolyether ester being made up of short-chain ester units;

the liquid permeability of said film being a maximum of 0.02 g/cm$^2$/h at 23°C. and 0.07 bar;

the percentage by weight of the long-chain ester units in the copolyether ester being 5–55%, and the average carbon to oxygen ratio of the long-chain glycols being 2.0 to 3.7 and the molecular weight thereof being 800–6000 with the proviso that if the average atomic ratio of carbon to oxygen of the long-chain glycols is 2.0 to 2.4, the percentage by weight of the long-chain ester units is 5–35;

the copolyether ester film being manufactured by at least one process selected from the group consisting of flat-sheet extrusion from polymer chips and extrusion blow molding from polymer chips, said polymer chips exhibiting a water absorption in 23°C. water of at most 15 weight %, referred to the dry weight of the chips.

2. An absorbent sanitary product according to claim 1, wherein the bibulous layer has a liquid absorption of at least 5 g/g, measured according to DIN 53923, a retention capacity of at least 3 g/g according to the Demand Wettability Test, and rewetting of at most 10% of an absorbed liquid.

3. An absorbent sanitary product according to claim 2, wherein the bibulous layer contains polymers having a very high water absorption capacity.

4. An absorbent sanitary product according to claim 1, wherein said long-chain glycol is a polyalkylene oxide glycol having a molecular weight of 1000 to 5000.

5. An absorbent sanitary product according to claim 1, wherein said short-chain ester units consist essentially of polybutylene terephthalate groups.

6. An absorbent sanitary product according to claim 1, wherein a thickness of the copolyether ester film is 5 to 35 μ.

7. An absorbent sanitary product according to claim 6, wherein said thickness is 10–20 μ.

8. An absorbent sanitary product according to claim 1, wherein said polymer chips have a water absorption of at most 12 weight %.

* * * * *

UNITED STATES PATENT AND TRADEMARK OFFICE
CERTIFICATE OF CORRECTION

PATENT NO. : 4,938,752

DATED : July 3, 1990

INVENTOR(S) : Cornelius M.F. VROUENRAETS et al

It is certified that error appears in the above-identified patent and that said Letters Patent is hereby corrected as shown below:

IN THE SPECIFICATION:

Col. 1, line 34, change "2.0 ." to --2.0.--;

line 66, change "µ," to --µm,-- (both occurrences).

Col. 2, line 2 change "µ)" to --µm)--.

Col. 3, line 36, change "lowmolecular-weight" to --low-molecular-weight--.

Col. 4, line 68, change "lowmolecular-weight" to --low-molecular-weight--.

Col. 6, line 3, change "cm" to --µm--;

line 24, change ".15" to --15--.

Col. 8, line 42, change "µ" to --µm--;

line 43, change "µ" to --µm--.

UNITED STATES PATENT AND TRADEMARK OFFICE
CERTIFICATE OF CORRECTION

PATENT NO. : 4,938,752

DATED : July 3, 1990

INVENTOR(S) : Cornelius M.F. VROUENRAETS et al

It is certified that error appears in the above-identified patent and that said Letters Patent is hereby corrected as shown below:

IN THE CLAIMS:

Claim 6, col. 10, line 3, change "$\mu$" to --$\mu m$--.

Claim 7, col. 10, line 2, change "$\mu$" to --$\mu m$--.

Signed and Sealed this

Eleventh Day of June, 1991

*Attest:*

HARRY F. MANBECK, JR.

*Attesting Officer*  *Commissioner of Patents and Trademarks*